(12) United States Patent
Timoszyk (10) Patent No.: US 10,767,811 B2
(45) Date of Patent: Sep. 8, 2020

(54) BRAKE CONTROL SYSTEM FOR SUSPENSIONS

(71) Applicant: Stryker Corporation, Kalamazoo, MI (US)

(72) Inventor: Wojciech Kazimierz Timoszyk, Flower Mound, TX (US)

(73) Assignee: Stryker Corporation, Kalamazoo, MI (US)

( * ) Notice: Subject to any disclaimer, the term of this patent is extended or adjusted under 35 U.S.C. 154(b) by 196 days.

(21) Appl. No.: 15/437,762

(22) Filed: Feb. 21, 2017

(65) Prior Publication Data

US 2017/0241587 A1 Aug. 24, 2017

Related U.S. Application Data

(60) Provisional application No. 62/299,172, filed on Feb. 24, 2016.

(51) Int. Cl.
| | | |
|---|---|---|
| *F16M 13/02* | (2006.01) | |
| *F16D 65/18* | (2006.01) | |
| *F21V 21/26* | (2006.01) | |
| *A61B 90/35* | (2016.01) | |
| *F21S 8/04* | (2006.01) | |
| *F16D 121/22* | (2012.01) | |
| *F21W 131/20* | (2006.01) | |

(52) U.S. Cl.
CPC ........... *F16M 13/022* (2013.01); *A61B 90/35* (2016.02); *F16D 65/183* (2013.01); *F21S 8/043* (2013.01); *F21V 21/26* (2013.01); *F16D 2121/22* (2013.01); *F16M 2200/06* (2013.01); *F21W 2131/20* (2013.01)

(58) Field of Classification Search
CPC .. A61B 2017/00398; A61B 2090/5025; A61B 6/4464; A61B 90/50; F16D 65/183; F16M 11/048; F16M 11/08; F16M 11/10; F16M 11/2007; F16M 11/2064; F21V 21/26
See application file for complete search history.

(56) References Cited

U.S. PATENT DOCUMENTS

| 4,223,222 A | * | 9/1980 | Gray | A61B 6/447 |
| | | | | 250/363.08 |
| 4,517,632 A | * | 5/1985 | Roos | F21V 21/403 |
| | | | | 188/163 |
| 4,548,373 A | * | 10/1985 | Komura | A61B 6/105 |
| | | | | 188/171 |

(Continued)

FOREIGN PATENT DOCUMENTS

WO WO 2015/070947 A1 5/2015

*Primary Examiner* — Tsion Tumebo
(74) *Attorney, Agent, or Firm* — Morrison & Foerster LLP (57) ABSTRACT

A medical device assembly including a support member, a first arm rotatably connected to the support member at a first rotary axis, a second arm rotatably connected to the first arm at a second rotary axis, and a medical unit connected to an end of the second arm opposite the first arm. The first arm is prevented from rotating about the first rotary axis when the first arm and the second arm are substantially aligned. The first arm and/or the second arm can also be prevented from rotating to prevent the medical device assembly from abutting against an obstacle.

40 Claims, 7 Drawing Sheets

(56) References Cited

U.S. PATENT DOCUMENTS

| | | | | |
|---|---|---|---|---|
| 4,894,855 A * | 1/1990 | Kresse | A61B 6/032 | 378/189 |
| 5,038,261 A * | 8/1991 | Kloos | F21V 21/14 | 362/286 |
| 6,012,821 A * | 1/2000 | Yeaney | F16M 11/10 | 248/325 |
| 6,343,601 B1 * | 2/2002 | Kiske | A61G 12/002 | 128/200.24 |
| 6,431,515 B1 | 8/2002 | Gampe et al. | | |
| 6,434,329 B1 * | 8/2002 | Dube | F16M 11/126 | 128/897 |
| 6,466,432 B1 * | 10/2002 | Beger | A61B 50/10 | 128/920 |
| 6,639,789 B2 * | 10/2003 | Beger | A61B 90/50 | 248/276.1 |
| 6,793,380 B2 | 9/2004 | Kupfer | | |
| 6,817,585 B2 * | 11/2004 | Wagner | F16M 11/10 | 248/324 |
| 7,073,765 B2 * | 7/2006 | Newkirk | A61M 16/0051 | 248/283.1 |
| 7,097,145 B2 * | 8/2006 | Turner | F16M 11/10 | 248/274.1 |
| 7,254,850 B2 | 8/2007 | Newkirk et al. | | |
| 7,676,865 B2 * | 3/2010 | Graham | A61G 7/0503 | 248/158 |
| 7,770,247 B2 | 8/2010 | Lubbers et al. | | |
| 7,770,860 B1 * | 8/2010 | Culpepper | A61G 12/002 | 248/324 |
| 7,849,978 B2 | 12/2010 | Graham et al. | | |
| 7,921,489 B2 * | 4/2011 | Newkirk | A61M 5/1415 | 137/355.16 |
| 8,141,188 B2 * | 3/2012 | Lubbers | F16D 63/008 | 5/658 |
| 8,888,696 B2 * | 11/2014 | Marka | A61B 90/35 | 600/249 |
| 9,195,022 B2 * | 11/2015 | Miladinovic | F16M 11/10 | |
| 9,687,305 B2 * | 6/2017 | Weller | A61B 90/35 | |
| 9,737,452 B2 * | 8/2017 | Lubbers | F16D 63/008 | |
| 9,750,470 B2 * | 9/2017 | Jun | A61B 6/145 | |
| 2002/0014562 A1 * | 2/2002 | Twisselmann | F16M 11/18 | 248/123.11 |
| 2003/0021107 A1 * | 1/2003 | Howell | E04B 9/006 | 362/147 |
| 2004/0178312 A1 * | 9/2004 | Parsons | A61G 15/10 | 248/276.1 |
| 2004/0262484 A1 * | 12/2004 | Wagner | F16M 11/10 | 248/324 |
| 2006/0207026 A1 * | 9/2006 | Newkirk | A61G 7/0503 | 5/600 |
| 2006/0226333 A1 * | 10/2006 | Newkirk | A61M 16/0051 | 248/647 |
| 2007/0007418 A1 * | 1/2007 | Lubbers | F16D 63/008 | 248/326 |
| 2010/0204578 A1 * | 8/2010 | Schmidt | A61B 8/4218 | 600/443 |
| 2013/0205558 A1 * | 8/2013 | Sporer | F16C 11/10 | 29/407.01 |
| 2013/0313382 A1 * | 11/2013 | Jakubczak | F16M 11/10 | 248/124.1 |
| 2014/0268751 A1 | 9/2014 | Boccoleri et al. | | |
| 2015/0184779 A1 | 7/2015 | Timoszyk et al. | | |
| 2016/0091117 A1 | 3/2016 | Boccoleri et al. | | |
| 2016/0296297 A1 | 10/2016 | Perplies et al. | | |

* cited by examiner

BRAKE CONTROL SYSTEM FOR SUSPENSIONS

CROSS REFERENCE TO RELATED APPLICATION

This claims the benefit of U.S. Provisional Application Ser. No. 62/299,172, filed Feb. 24, 2016.

FIELD OF THE INVENTION

The present invention relates to surgical devices, and in particular to a smart brake for an arm of a surgical device.

BACKGROUND OF THE INVENTION

Surgical monitors have been used in operating rooms to provide images to surgeons in the room. Likewise, other wired surgical devices, such as speakers, joysticks, keyboards and cameras, have been used in operating rooms to provide information to a surgeon or other person in the operating room (e.g., images from a camera or patient vital information). Moreover, surgical lights have been used in operating rooms to provide increased light to a specific area of the room. For example, the surgical light can be positioned within an operating room and can provide increased light to a specific area of a person being operated on within the operating room.

It is desired to have an easier way to position the surgical devices.

SUMMARY OF THE INVENTION

The present invention, according to one aspect, is directed to a medical device assembly including a support member, a first arm rotatably connected to the support member at a first rotary axis, a second arm rotatably connected to the first arm at a second rotary axis, and a medical unit connected to an end of the second arm opposite the first arm. The first arm is prevented from rotating about the first rotary axis when the first arm and the second arm are substantially aligned.

Another aspect of the present invention is to provide a medical device assembly including a ceiling support member, a substantially linear first arm and a substantially linear second arm. The substantially linear first arm has a first arm first end and a first arm second end, with the first arm first end of the substantially linear first arm being rotatably connected to the ceiling support member at a first rotary joint for allowing the substantially linear first arm to rotate about a first substantially vertical axis. The substantially linear second arm has a second arm first end and a second arm second end, with the second arm first end of the substantially linear second arm being rotatably connected to the substantially linear first arm at a second rotary joint for allowing the substantially linear second arm to rotate about a substantially vertical second axis. The substantially linear first arm is prevented from rotating about the first substantially vertical axis when the substantially linear first arm and the substantially linear second arm are substantially aligned such that a first line extending between the first arm first end and the first arm second end of the substantially linear first arm is substantially parallel with a second line extending between the second arm first end and the second arm second end of the substantially linear second arm.

Yet another aspect of the present invention is to provide a method of moving a surgical device assembly. The method includes providing a ceiling support member, providing a substantially linear first arm having a first arm first end and a first arm second end, with the first arm first end of the substantially linear first arm being rotatably connected to the ceiling support member at a first rotary joint for allowing the substantially linear first arm to rotate about a first substantially vertical axis, and providing a substantially linear second arm having a second arm first end and a second arm second end, with the second arm first end of the substantially linear second arm being rotatably connected to the substantially linear first arm at a second rotary joint for allowing the substantially linear second arm to rotate about a substantially vertical second axis. The method further includes preventing the substantially linear first arm from rotating about the first substantially vertical axis when the substantially linear first arm and the substantially linear second arm are substantially aligned such that a first line extending between the first arm first end and the first arm second end of the substantially linear first arm is substantially parallel with a second line extending between the second arm first end and the second arm second end of the substantially linear second arm. The method also includes allowing the substantially linear first arm to rotate about the first substantially vertical axis when the substantially linear first arm and the substantially linear second arm are not substantially aligned.

Another aspect of the present invention is to provide a method of moving a surgical device assembly including providing a support member, providing a support arm assembly having a proximal end and a distal end, with the support arm assembly including a plurality of support arms, rotatably connecting the proximal end of the support arm assembly to the support member for rotation about a proximal pivot joint axis, connecting the distal end of the support arm to a medical unit, rotatably connecting each of the support arms to at least one of the support arms, each of the support arms being rotatably connected to the at least one of the support arms for rotation about an intermediate pivot joint axis, measuring a proximal angle of the support arm assembly relative to the support member about the proximal pivot joint axis, measuring each intermediate angle of each of the support arms about each intermediate pivot joint axis, and preventing the support arm assembly from rotating about the proximal pivot joint axis and the support arms from rotating about each intermediate pivot joint axis when at least the proximal angle and each intermediate angle indicate that the medical unit is at a certain location.

Yet another aspect of the present invention is to provide a medical device assembly including a support member and a support arm assembly having a proximal end and a distal end, with the support arm assembly including a plurality of support arms. The proximal end of the support arm assembly is rotatably connected to the support member for rotation about a proximal pivot joint axis. The distal end of the support arm is connected to a medical unit. Each of the support arms are rotatably connected to at least one of the support arms, with each of the support arms being rotatably connected to the at least one of the support arms for rotation about an intermediate pivot joint axis. The medical device assembly further includes a proximal angle measurement system for measuring a proximal angle of the support arm assembly relative to the support member about the proximal pivot joint axis and an intermediate angle measurement system for measuring each intermediate angle of each of the support arms about each intermediate pivot joint axis. The support arm assembly is prevented from rotating about the proximal pivot joint axis and the support arms is prevented from rotating about each intermediate pivot joint axis when at least the proximal angle and each intermediate angle indicate that the medical unit is at a certain location.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

The specific devices and processes illustrated in the attached drawings, and described in the following specification are simply exemplary embodiments of the inventive concepts. Hence, specific dimensions and other physical characteristics relating to the embodiments disclosed herein are not to be considered as limiting.

DETAILED DESCRIPTION

For purposes of description herein, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The reference number 10 (FIGS. 1-2) generally designates a suspension arm assembly of the present invention. The suspension arm assembly 10 includes a ceiling attachment member 12, a medical unit 14 and an arm arrangement 16 between the ceiling attachment member 12 and the medical unit 14. The illustrated suspension arm assembly 10 is configured to be positioned within a room (e.g., an operating room) and, in the illustrated embodiment, includes the medical unit 14, which is configured to provide information to the medical personnel in the room and/or to assist the medical personnel in the room in performing various functions (e.g., supporting equipment and providing gas, electrical power and data connectivity). In the illustrated example, the medical unit 14 is a surgical light assembly 18 including a surgical light 20 and a surgical light support arm 22 for providing increased light to a specific area of a person being operated on within the operating room. However, the medical unit 14 could be any device configured to be connected to the end of the arm arrangement 16. For example, the medical unit 14 could be a display support assembly for supporting a display monitor for providing surgical information to a surgeon or other person in the operating room (e.g., images from a camera (e.g., an in-light camera or an endoscopic camera) or patient vital information). It is contemplated that other items (e.g., dual displays, service head, cameras, microphones, etc.) in addition to or instead of the surgical light assembly 18 can be located at the end of the suspension arm assembly 10. If the medical unit 14 is a surgical light 20, the surgical light 20 could be any surgical light 20. For example, the surgical light 20 could include the housing, light source and optics of U.S. Patent Application Publication No. 2014/0268751 entitled SURGICAL LIGHT WITH BEAM REDIRECTING OPTICS, the entire contents of which are incorporated herein by reference.

Figure 1:
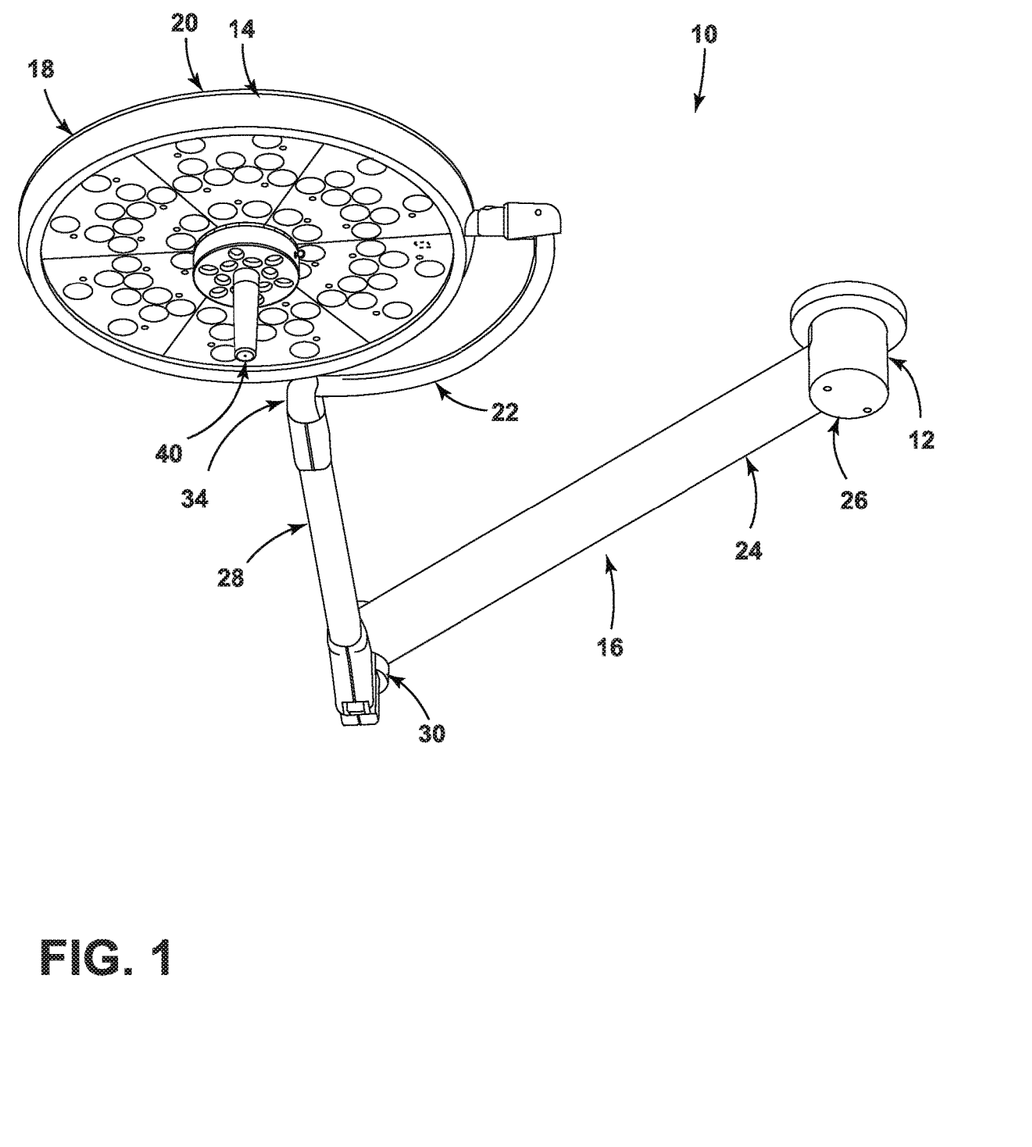
FIG. 1 is a perspective view of a suspension arm assembly of the present invention.
Figure 2:
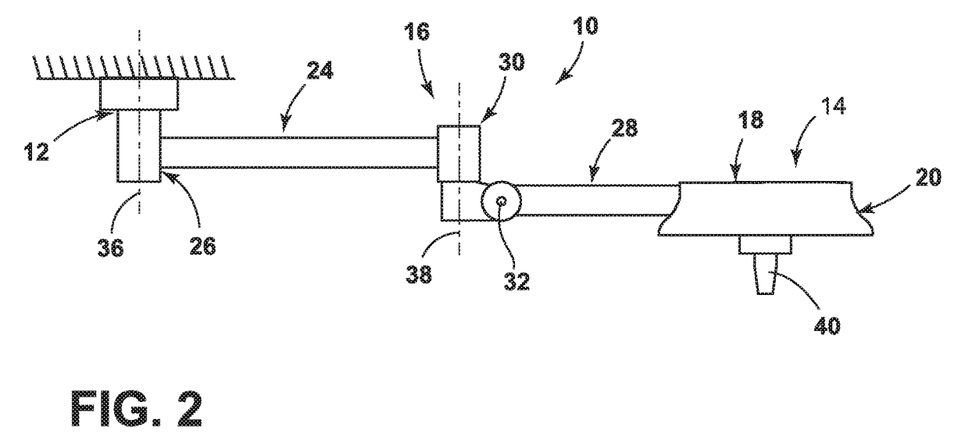
FIG. 2 is a side view of the suspension arm assembly of the present invention.

In the illustrated example, the suspension arm assembly 10 is connected to a ceiling and supports the medical unit 14 above a support surface, such as a floor. The suspension arm assembly 10 includes the ceiling attachment member 12, a first arm 24 connected to the ceiling attachment member 12 at a first rotation joint 26, a second arm 28 connected to the first arm 24 by a second rotation joint 30, and the surgical light assembly 18 connected to an end of the second arm 28. It is contemplated that the second arm 28 could be a load counterbalancing spring arm that allows the second arm 28 to rotate about a horizontal axis 32 adjacent the second rotation joint 30. The surgical light assembly 18 can be connected to the second arm 28 with a third rotation joint 34. The joints 26, 30 and 34 can be infinite to allow for unlimited rotation. For example, the joints can be an infinite rotation joint as disclosed in U.S. Patent Application Publication No. 2016/0091117 entitled FIBER OPTIC AND SLIP RING ROTARY JOINT FOR SUSPENSION ARM, the entire contents of which are hereby incorporated herein by reference. The joints 26, 30 and 34 can also be joints of limited rotation. For example, the joints 26, 30 and 34 can be the joints of U.S. Patent Application Publication No. 2015/0184779 entitled MULTI-STAGE ROTARY OVERTRAVEL STOP, the entire contents of which are hereby incorporated herein by reference. Moreover, while the suspension arm assembly 10 includes the ceiling attachment member 12 for connecting the suspension arm assembly 10 to a ceiling, it is contemplated that the ceiling attachment member 12 could be used to connect the suspension arm assembly 10 to any structure (fixed or movable) above a support surface, such as a floor.

In the illustrated example, the arm arrangement 16 of the suspension arm assembly 10 allows the medical unit 14 to be moved to a desired position. For example, when the medical unit 14 is the surgical light assembly 18, the arm arrangement 16 can be moved such that light from the surgical light assembly 18 can be pointed at a certain area within the operating room. As illustrated in FIG. 2 and as shown schematically in FIG. 3, the first arm 24 of the suspension arm assembly 10 pivots relative to the ceiling attachment member 12 about a first vertical axis 36 at the first rotation joint 26 and the second arm 28 of the suspension arm assembly 10 pivots relative to the first arm 24 about a second vertical axis 38 at the second rotation joint 30, with the first vertical axis 36 being substantially parallel to the second vertical axis 38. The medical unit 14 attached to the end of the second arm 28 can be moved to a selected position by rotating the first arm 24 about the first vertical axis 36 and/or rotating the second arm 28 about the second vertical axis 38. The medical unit 14 can include further axes for moving the medical unit 14 to a desired position or for orientating to point the medical unit 14 toward a desired location (e.g., for a surgical light or camera). The medical unit 14 typically includes at least one handle (e.g., a handle 40 extending from the surgical light 20 as illustrated in FIGS. 1 and 2). The suspension arm assembly 10 can include a button, a capacitive sensor, a proximity switch/sensor (or similar) (e.g., on the handle 40 of the medical unit 14) that is depressed to allow free movement of the first arm 24 and the second arm 28, subject to the limitations outlined below. It is also contemplated that the suspension arm assembly 10 could include a force sensor that detects when a force is applied to the second arm 28 signifying that movement of the medical unit 14 is desired, thereby unlocking all joints subject to the limitations outlined below.

Figure 3:
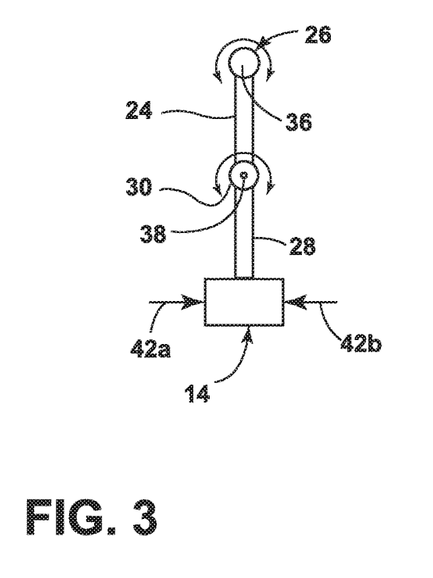
FIG. 3 is a schematic top view of the suspension arm assembly of the present invention.
Figure 4A:
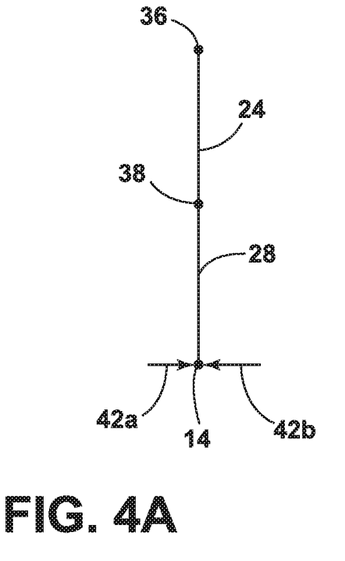
FIG. 4A illustrates a schematic top view of the suspension arm assembly of the present invention with a first arm of the suspension arm assembly being substantially aligned with a second arm of the suspension arm assembly.

FIGS. 2, 3 and 4A illustrate a situation wherein the first arm 24 and the second arm 28 are substantially positioned along a line. In this position, an angle α as shown schematically in FIG. 4A between the first arm 24 and the second arm 28 about the second vertical axis 38 is 180°. When the first arm 24 and the second arm 28 are so aligned, it may be difficult to properly move the medical unit 14 to a desired position.

Figure 4B:
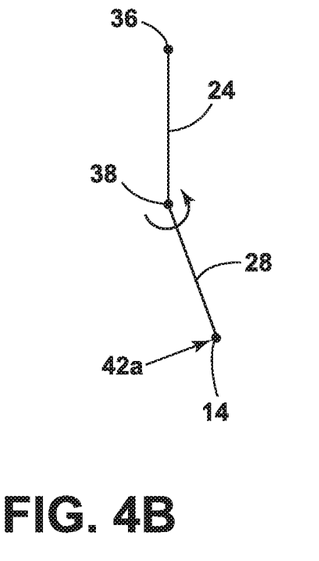
FIG. 4B illustrates a schematic top view of the suspension arm assembly of the present invention showing movement of the first arm relative to the second arm of the suspension arm assembly.
Figure 4C:
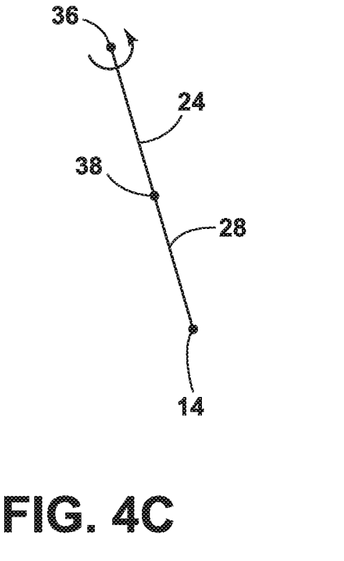
FIG. 4C illustrates a schematic top view of the suspension arm assembly of the present invention showing movement of the first arm with the second arm of the suspension arm assembly.
Figure 4D:
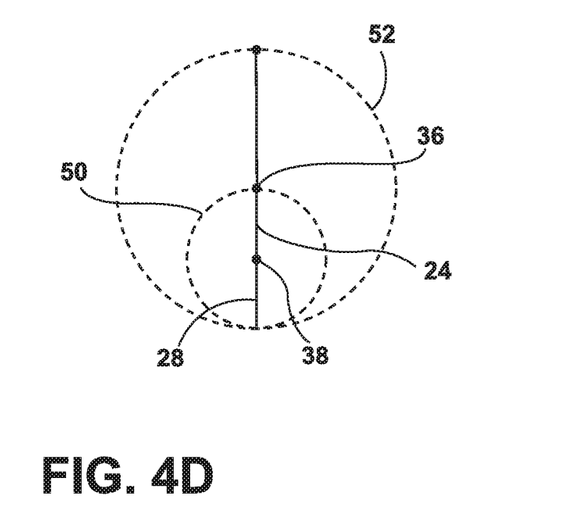
FIG. 4D illustrates a schematic range of motion of the first arm and the second arm of the suspension arm assembly of the present invention.

FIGS. 3 and 4A illustrate when a force 42a, 42b is applied to the medical unit 14 in a direction substantially perpendicular to the line along the aligned first arm 24 and second arm 28. In this situation, precise desired movement of the medical unit 14 can be difficult because rotation about the first vertical axis 36 may occur when rotation about the second vertical axis 38 is desired or rotation about the second vertical axis 38 may occur when rotation about the first vertical axis 36 is desired. FIG. 4B illustrates movement of the arm arrangement 16 when the force 42a forces the second arm 28 to pivot relative to the first arm 24 about the second vertical axis 38. Such movement will force the medical unit 14 to move in a first circle 50 (shown in FIG. 4D) about the second vertical axis 38. FIG. 4C illustrates movement of the arm arrangement 16 when the force 42a forces the first arm 24 and second arm 28 to pivot relative to the ceiling attachment member 12 about the first vertical axis 36. Such movement will force the medical unit 14 to move in a second circle 52 (shown in FIG. 4D) about the first vertical axis 36. When the first arm 24 and the second arm 28 are so aligned, the arm arrangement 16 may move according to FIG. 4B or may move according to FIG. 4C, possibly thereby creating a frustrating situation for the user of the suspension arm assembly 10 if such movement does not directly result in predictable and desired movement of the medical unit 14.

Figure 4E:
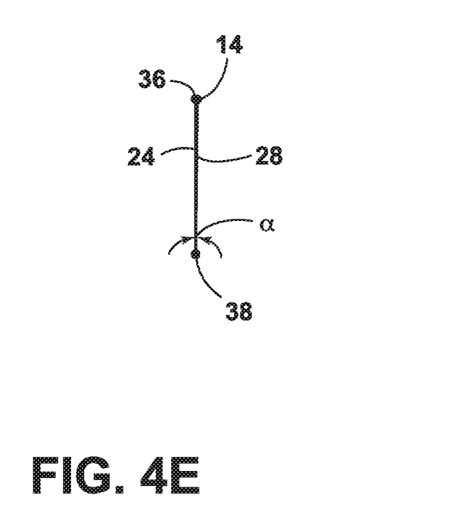
FIG. 4E illustrates a schematic top view of the suspension arm assembly of the present invention with the first arm being aligned and over the second arm of the suspension arm assembly.

FIG. 4E illustrates a situation similar to the situation in FIG. 4A as outlined above, wherein the first arm 24 and the second are 28 are also substantially in a line, but with the angle α between the first arm 24 and the second arm 28 about the second vertical axis 38 being approximately 0°. When the angle α between the first arm 24 and the second arm 28 about the second vertical axis 38 is approximately 0°, the first arm 24 and the second arm 28 are also positioned substantially along a line (e.g., the same line). In this situation, the force 42a, 42b applied to the medical unit 14 in a direction substantially perpendicular to the line along which the aligned first arm 24 and the second arm 28 are positioned may also move the first arm 24 about the first vertical axis 36 or may move the second arm 28 about the second vertical axis 38, once again thereby possibly creating a frustrating situation for the user of the suspension arm assembly 10 if such movement does not directly result in predictable and desired movement of the medical unit 14.

An aspect of the present invention is to provide for predictable movement of the arm arrangement 16. In an aspect of the present invention, the first arm 24 of the arm arrangement 16 will be locked in position to prevent the arm arrangement 16 from pivoting about the first vertical axis 36 until the first arm 24 is no longer substantially aligned with the second arm 28. Therefore, when the force 42a or 42b is applied to the medical unit 14, the arm arrangement 16 will not be able to rotate about the first vertical axis 36, thereby locking the first arm 24 in position. The second arm 28 will therefore pivot about the second vertical axis 38 (as shown in FIG. 4B) until the angle α between the first arm 24 and the second arm 28 is a selected amount above or below 180° and a selected amount above or below 0°. For example, the first arm 24 can be locked into position relative to the ceiling attachment member 12 until the angle α between the first arm 24 and the second arm 28 is 5-10° above or below 180° and 0°. Once the angle α between the first arm 24 and the second arm 28 is in the range of 5°-175° or in the range of 185°-355° (or in the range of 10°-170° or in the range of 190°-350° if the 10° range is selected) in the present example, the first arm 24 is released and both the first arm 24 is free to pivot about the first vertical axis 36 and the second arm 28 is free to pivot about the second vertical axis 38. Because of the non-alignment of the first arm 24 and the second arm 28 at that point, the medical unit 14 is easily moved to a desired position. It is contemplated that the first arm 24 could be locked only when the angle α between the first arm 24 and the second arm 28 is close to 180° or only when the angle α is close to 0°, or when the angle α is either close to 180° or close to 0° as outlined above.

In the illustrated example, the angle α between the first arm 24 and the second arm 28 is measured to determine when to lock the first arm 24 in position relative to the ceiling attachment member 12 to prevent rotation of the first arm 24 about the first vertical axis 36. It is contemplated that the angle α could be measured in any manner. For example, the angle α could be measured using any electrical or mechanical system or a combination thereof. The angle α could be determined using an encoder on one of the first arm 24 or the second arm 28 and a reader on the other of the first arm 24 or the second arm 28 for reading a rotated position of the first arm 24 relative to the second arm 28.

Figure 5:
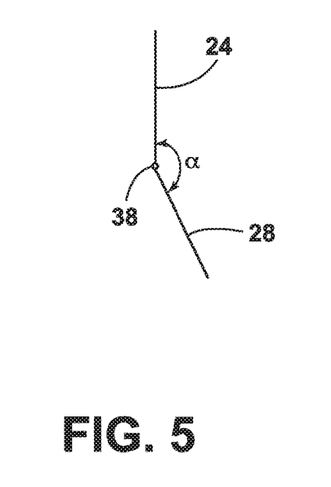
FIG. 5 illustrates a schematic top view of the suspension arm assembly of the present invention showing the angle between the first arm and the second arm of the suspension arm assembly.
Figure 6:
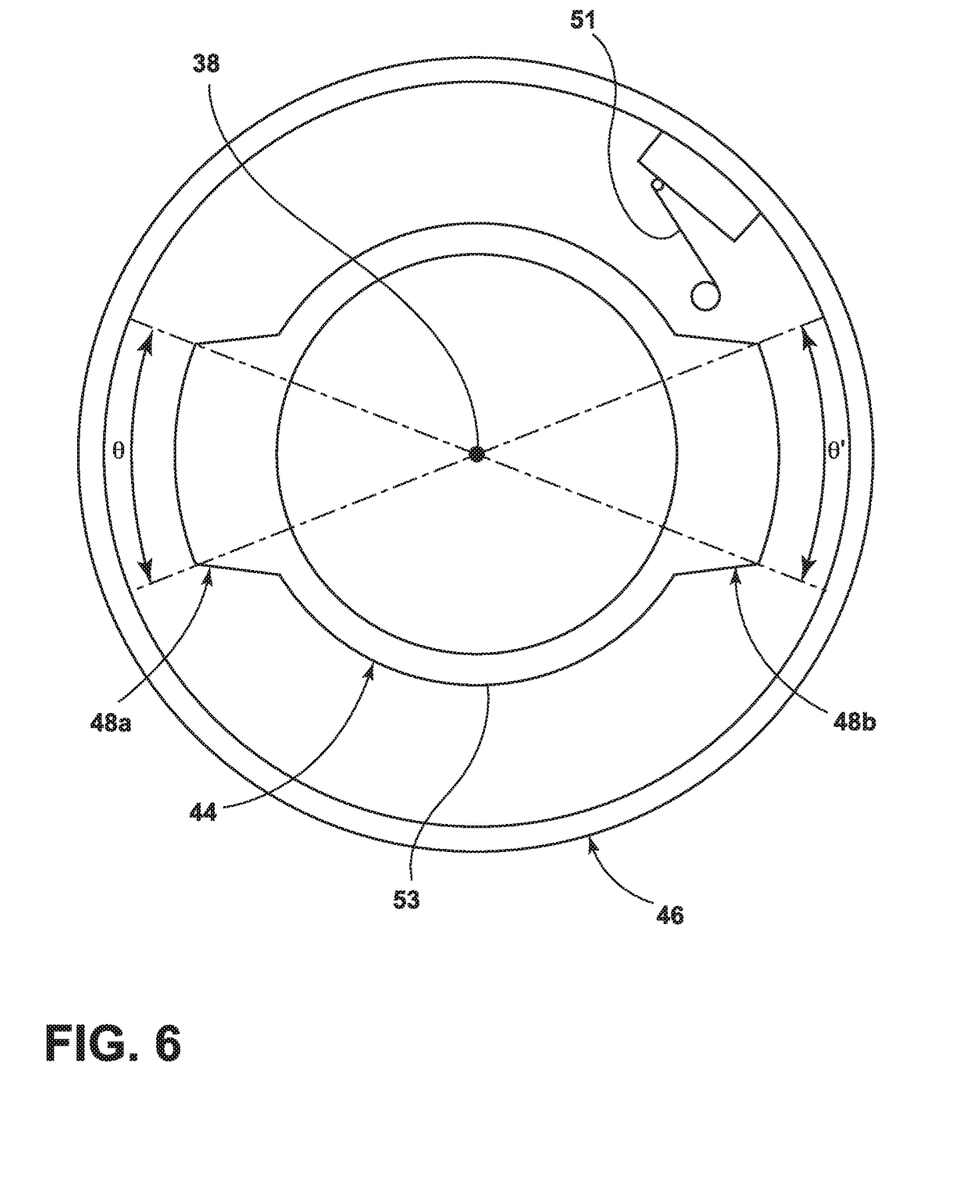
FIG. 6 illustrates a cross-sectional view of an embodiment of a joint between the first arm and the second arm of the suspension arm assembly of the present invention.

FIG. 6 illustrates an example of an electro/mechanical system for determining the angle α. As shown in FIG. 5, an inner member 44 of one of the first arm 24 and the second arm 28 rotates within an outer member 46 of the other of the first arm 24 and the second arm 28 at the second rotation joint 30 about the second vertical axis 38. Any wiring passing through the arm arrangement 16 from the ceiling attachment member 12 to the medical unit 14 can pass through the inner member 44. The inner member 44 is configured to rotate within the outer member 46 in any manner known to those skilled in the art. In the illustrated example, an outer surface 53 of the inner member 44 includes a first cam 48a and a second cam 48b. The outer member 46 includes a switch arm 51 that is configured to abut each of the cams 48a, 48b as the cams 48a, 48b pass the switch arm 51. When the cams 48a, 48b abut the switch arm 51, the switch arm 51 will deflect to thereby complete a circuit (or open a circuit). When the circuit is completed (or opened), a control system for the suspension arm assembly 10 will know that the angle α between the first arm 24 and the second arm 28 is at the selected amount above or below 180° for a first one of the cams 48a and the selected amount above or below 0° for a second one of the cams 48b to thereby lock the first arm 24 in position relative to the ceiling attachment member 12 to prevent rotation of the first arm 24 about the first vertical axis 36. The second arm 28 can then be rotated until the angle α between the first arm 24 and the second arm 28 is outside the selected amount above or below 180° or the selected amount above or below 0° to thereby unlock the first arm 24 and allow the first arm 24 to rotate (when the cams 48a, 48b no longer engage the switch arm 51 and the circuit is no longer complete). The first one of the cams 48a has an angular distance of e degrees corresponding to the selected amount above or below 180° and the second one of the cam 48b has an angular distance of θ' degrees corresponding to the selected amount above or below 0° such that the cams 48a, 48b will abut the switch arm 51 when angle α between the first arm 24 and the second arm 28 is the selected amount above or below 180° or the selected amount above or below 0°. It is contemplated that the cams 48a, 48b could be replaced by an electrical, optical or magnetic element that could be sensed by a sensor in place of the switch arm 51. Moreover, it is contemplated that the sensed element and the sensor could be on either the first arm 24 or the second arm 28 or on the inner member 44 and the outer member 46 (e.g., the cams 48a, 48b on an inner surface of the outer member 46 and the switch arm 51 on the outer surface 53 of the inner member 44).

In the illustrated example, the first arm 24 can be locked in position to prevent the arm arrangement 16 from pivoting about the first vertical axis 36 until the first arm 24 is no longer substantially aligned with the second arm 28 in any manner. For example, it is contemplated that the handle 40 could employ a capacitance touch system under control of a control system of the medical unit 14 to lock the arm arrangement 16 in a selected position once the handle 40 is released. A capacitance touch system that releases all joint locks (e.g, those between the first arm 24 and the ceiling attachment member 12 at the first vertical axis 36 and between the first arm 24 and the second arm 28 at the second vertical axis 38) when the handle 40 is grasped and that locks all joint locks when the handle 40 is released is described in U.S. Pat. No. 4,517,632 entitled OPERATING THEATRE LAMP, the entire contents of which are incorporated herein by reference. If the suspension arm assembly 10 employs the capacitance touch system, it is contemplated that the capacitance touch system could be used to lock the first arm 24 to prevent rotation about the first vertical axis 36 when the angle α between the first arm 24 and the second arm 28 is close to 180° and/or 0° as outlined above.

The illustrated suspension arm assembly 10 could include more than two arms 24, 28. For example, it is contemplated that the suspension arm assembly 10 could include any number of arms. If the suspension arm assembly 10 has more than two arms, it is contemplated that the joints between the arms will lock outward from the main pivot point (e.g., at the ceiling or other support structure for the suspension arm assembly 10) when the arms of the suspension arm assembly 10 are substantially aligned. For example, if the suspension arm assembly 10 includes three arms, when the three arms are substantially aligned, the first rotation joint between the main pivot point and the first arm along with the second rotation joint between the first arm and the second arm would lock in position while a third rotation joint between the second arm and a third arm would be allowed to move. Once the angle between the second arm and the third arm is outside the selected amount above or below 180° or the selected amount above or below 0°, the second rotation joint would be unlocked and allowed to rotate. Thereafter, once the angle between the first arm and the second arm is outside the selected amount above or below 180° or the selected amount above or below 0°, the first rotation joint would be unlocked and allowed to rotate. It is also contemplated that the medical unit 14 could have a rotational joint at the connection to the second arm (or terminal arm of the suspension arm assembly 10).

The reference numeral 10a (FIG. 7) generally designates another embodiment of the present invention, having a second embodiment for the suspension arm assembly. Since suspension arm assembly 10a is similar to the previously described suspension arm assembly 10, similar parts appearing in FIG. 1 and FIG. 7, respectively, are represented by the same, corresponding reference number, except for the suffix "a" in the numerals of the latter. Another aspect of the present invention is to provide a system that at least temporarily stops movement of the suspension arm assembly 10a to prevent the medical unit 14a and/or the arm arrangement 16a from abutting a nearby fixed obstacle or from passing into a prohibited area. As outlined above, the medical unit 14a can provide information to the medical personnel in a room 100 and/or to assist the medical personnel in the room 100 in performing various functions (e.g. a service head, a monitor and/or a surgical light).

Figure 7:
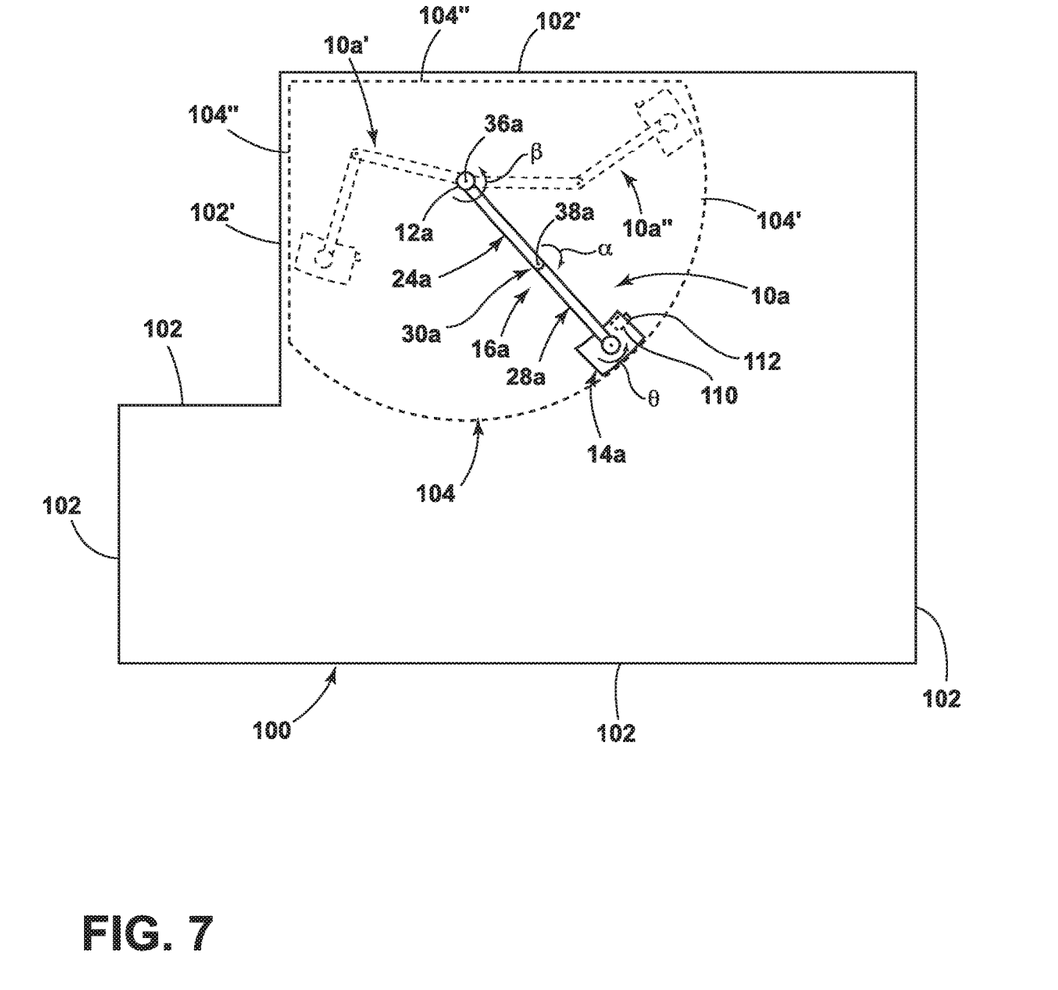
FIG. 7 illustrates a top schematic view of a second embodiment of the suspension arm assembly of the present invention in a room.

FIG. 7 illustrates a top schematic view of the suspension arm assembly 10a in the room 100. The room 100 has a plurality of walls 102 including a pair of walls 102' adjacent the suspension arm assembly 10a. If the medical unit 14a was allowed to freely move, the medical unit 14a and/or the arm arrangement 16a would abut the walls 102' adjacent the suspension arm assembly 10a. The illustrated suspension arm assembly 10a is prevented from passing outside of a movement zone 104. The movement zone 104 is defined by a motion limit zone 104' that is substantially a portion of circle centered on the first vertical axis 36a where the arm arrangement 16a rotates about the ceiling (or other support) attachment member 12a. The motion limit zone 104' is defined by an area wherein the arm arrangement 16a is fully extended (i.e., when all arms of the arm arrangement 16a are parallel (shown in solid lines in FIG. 7)). The movement zone 104 also includes an abutment safety zone 104" that is spaced from the walls 102' adjacent the suspension arm assembly 10a. Since the suspension arm assembly 10a is not able to pass through the abutment safety zone 104" of the movement zone 104, the suspension arm assembly 10a will not abut against the walls 102'. It is contemplated that the abutment safety zone 104" creates a barrier that prevents the suspension arm assembly 10a from moving into an area wherein the suspension arm assembly 10a would abut other items (e.g., a bed, a television or any other item in the room 100) or into an area wherein it is desirable to keep the suspension arm assembly 10a outside of for any reason.

Figure 8:
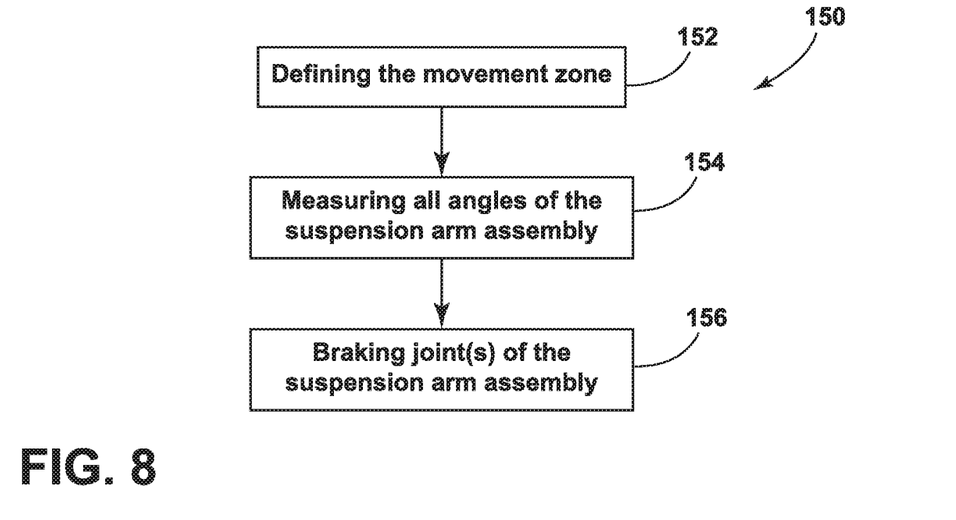
FIG. 8 illustrates a method of keeping the suspension arm assembly of the present invention within a movement zone.

In the illustrated example, a method 150 (FIG. 8) of keeping the suspension arm assembly 10a within the movement zone 104 includes a first step 152 of defining the movement zone 104, a second step 154 of measuring all angles of the suspension arm assembly 10a and a third step 156 of braking at least temporality some of the joints of the suspension arm assembly 10a.

The illustrated suspension arm assembly 10a includes a control system 110 having the movement zone 104 saved therein. The control system 110 is illustrated as being located in the medical unit 14a in FIG. 7. However, the control system 110 can be located anywhere in the suspension arm assembly 10a or could be located in an exterior device (e.g., in a wall in the room 100) that communicates with the suspension arm assembly 10a. The control system 110 is well known to those skilled in the art and can include a motherboard having one or more processors or other similar control devices as well as one or more memory devices. The processor controls the overall operation of the control system and can include hardwired circuitry, programmable circuitry that executes software, or a combination thereof. The processor may, for example, execute software stored in the memory device. The processor may include, for example, one or more general- or special-purpose programmable microprocessors and/or microcontrollers, application specific integrated circuits (ASICs), programmable logic devices (PLDs), programmable gate arrays (PGAs), or the like. The memory device may include any combination of one or more random access memories (RAMS), read-only memories (ROMs—which may be programmable), flash memory, and/or other similar storage devices.

In the illustrated example, the movement zone 104 can be defined in the first step 152 of the method 150 and saved in the control system 110 in any manner. For example, it is contemplated that the manufacturer of the suspension arm assembly 10a could know the dimensions of the room 100 including the walls 102 and 102', the location of the first vertical axis 36a, the length of all of the arms 24a, 28a, etc. of the arm arrangement 16a and the configuration of the medical unit 14a (including a peripheral shape and size thereof and whether the medical unit 14a is pivotally connected to the arm arrangement 16a). All of this information can be used to accurately define the movement zone 104, which is then saved in the control system 110. Alternatively, the movement zone 104 can be recorded and saved into the control system 110 after the suspension arm assembly 10a has been installed in the room 100. For example, a button 112 (e.g., a push button or on a touchscreen visible from the exterior of the suspension arm assembly 10a or hidden behind an access panel) interacting with the control system 110 can be actuated and the medical unit 14a can be moved about the periphery of the movement zone 104. For example, the button 112 can be actuated a first time when the suspension arm assembly 10a is positioned fully extended from the first vertical axis 36a (as shown in solid lines in FIG. 7), the suspension arm assembly 10a can then be moved along the motion limit zone 104' and the abutment safety zone 104" (shown as the suspension arm assembly 10a' in dashed lines in FIG. 7) until the suspension arm assembly 10a has moved along the entire periphery of the movement zone 104, and then the button 112 can be actuated a second time to thereby save the location of the periphery of the movement zone 104 in the control system 110. If the suspension arm assembly 10a includes the system for preventing the first arm 24a from rotating about the first vertical axis 36a when the first arm 24a and the second arm 28a are substantially aligned as discussed above in reference to FIGS. 1-7, then this system is temporarily disabled during actuation of the button 112 to record the movement zone 104 (thereby allowing the first arm 24a to rotate about the first vertical axis 36a while also allowing the first arm 24a to be substantially aligned with the second arm 28a). Any other method of saving the location of the movement zone 104 within the control system 110 can be used.

In the second step 154 of the method 150 of keeping the suspension arm assembly 10a within the movement zone 104, all angles of the suspension arm assembly 10a are measured. Accordingly, in the second step 154 of the method 150, the angle $\beta$ of the arm arrangement 16a about the first vertical axis 36a is measured, the angle $\alpha$ of the first arm 24a relative to the second arm 28a and the angle $\theta$ of the second arm 28a relative to the medical unit 14a. In some situations, the medical unit 14a will be fixed in position relative to the second arm 28a, such that the angle $\theta$ of the second arm 28a relative to the medical unit 14a will not have to be measured. It is further considered that the arm arrangement 16a could include more than two arms. When the arm arrangement 16a has more than two arms, the angles between each arm are also measured. Furthermore, additional angles could be measured (e.g., when the medical unit 14a has more than one axis of rotation relative to the end of the arm arrangement 16a (for example, when the medical unit 14a is a surgical light and the surgical light is connected to the arm arrangement 16a using the multiple axis surgical light support arm 22 as illustrated in FIG. 1)). Moreover, if the arms of the arm arrangement 16a are able to rotate about a horizontal axis relative to each other (or are able to bend about an internal horizontal axis), the angles of any horizontal axis can also be measured to determine the exact location of the arms of the arm arrangement 16a and the medical unit 14a.

Figure 9:
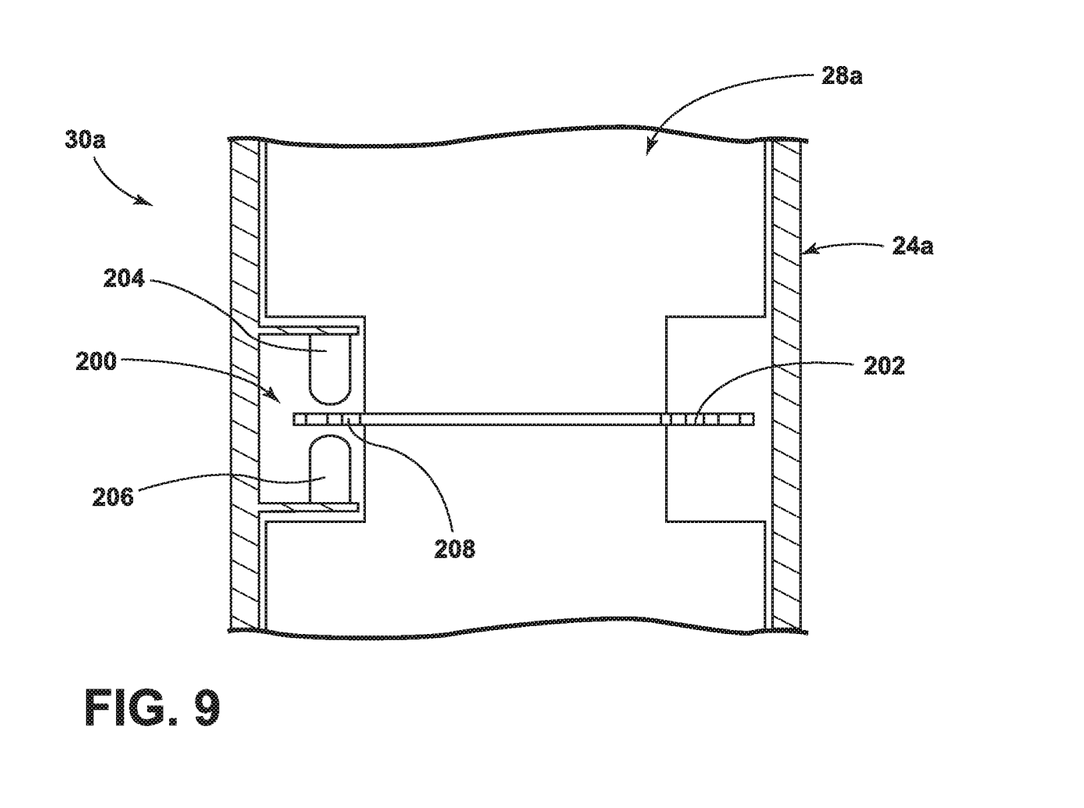
FIG. 9 illustrates a schematic of an angle encoder for use with the suspension arm assembly of the present invention.

In the illustrated example, the angles $\alpha$, $\beta$, $\theta$, etc. of the suspension arm assembly 10a can be measured in any manner. For example, the angles $\alpha$, $\beta$, $\theta$, etc. can be measured using a rotary encoder (e.g., mechanical, optical, magnetic, capacitive, inductive) or using a potentiometer for measuring the angles $\alpha$, $\beta$, $\theta$, etc. Such rotary encoders and potentiometers are well known to those skilled in the art. It is also contemplated that any other device or method of determining the angles $\alpha$, $\beta$, $\theta$, etc. could be used. By way of example, FIG. 9 illustrates an example of an optical rotary encoder system 200 at the second rotation joint 30a for measuring the angle $\alpha$ of the first arm 24a relative to the second arm 28a at the second vertical axis 38a. The illustrated optical rotary encoder system 200 including a rotary plate 202 connected to the second arm 28a, a light outputting LED array 204 connected to the first arm 24a and a photo detector array 206 connected to the first arm 24a. As is well known to those skilled in the art, the rotary plate 202 includes a plurality of slots or transparent areas 208 in different patterns on the rotary plate 202, with each unique pattern indicating a particular angle of the rotary plate 202. Light from the light outputting LED array 204 passes through the slots or transparent areas 208 and is read by the photo detector array 206. A controlling device for the photo detector array 206, such as a microprocessor or microcontroller, reads the optical pattern resulting from the angular position of the rotary plate 202 at any time to determine the angle α.

Figure 10:
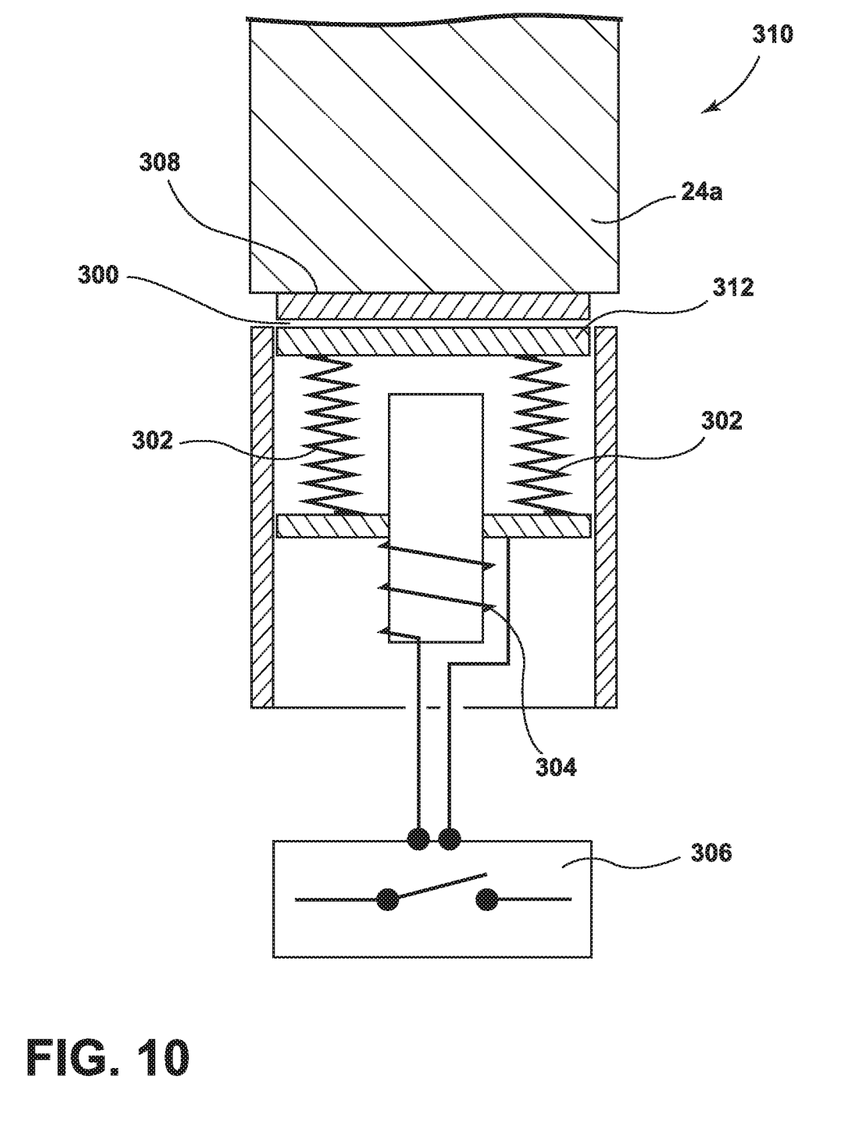
FIG. 10 illustrates a schematic of a brake system for use with the suspension arm assembly of the present invention.

In the third step 156 of the method 150 of keeping the suspension arm assembly 10a within the movement zone 104, at least some of the joints of the suspension arm assembly 10a are at least temporality braked to stop movement of the suspension arm assembly 10a. It is contemplated that the joints could be braked in any manner using any manner of braking known to those skilled in the art. For example, a brake system 310 of FIG. 10 could be used. The brake system 310 includes a brake surface 308 on the first arm 24a and cooperates with a brake pad 312 which is movable relative thereto and which is mounted on the second arm 28a. The brake pad 312 is normally pressed by springs 302 against the brake surface 308 so that the first arm 24a and the second arm 28a can only be moved relative to one another with difficulty or not at all. An electromagnet 304, which can be supplied with current and correspondingly energised on closing a switch 306, is arranged at a certain distance beneath the brake pad 312. On being energised, the electromagnet attracts the appropriately magnetically constructed brake pad 312 and releases it from the brake surface 308. The first arm 24a and the second arm 28a can easily be rotated relative to one another. On renewed opening of the switch 306 the brake pad 312 is again pressed by the springs 302 against the brake surface 308 and the first arm 24a and the second arm 28a are again essentially fixed relative to one another. Corresponding brakes are also provided at the remaining joints.

In the illustrated example, when a measurement of the angles α, β, θ, etc. during the second step 154 determines that the suspension arm assembly 10 is at the motion limit zone 104' or abutment safety zone 104", the joints of the suspension arm assembly 10 are braked to prevent the suspension arm assembly 10 from passing through the motion limit zone 104' or abutment safety zone 104". It is contemplated that the second rotation joint 30a between the first arm 24a and the second arm 28a could be at the abutment safety zone 104" without the medical unit 14a being at the abutment safety zone 104". For example, as shown in FIG. 7, the first arm 24a is longer than the distance between the first vertical axis 36a and the rear wall 102' of the room 100. Therefore, if the first arm 24a was rotated to such that the second rotation joint 30a is at the abutment safety zone 104", the brakes will be applied to at least the joint at the first vertical axis 36a to prevent movement of the first arm 24' into the rear wall 102'. In this situation, it is contemplated that other joints may not be braked. Therefore, during the method 150 of keeping the suspension arm assembly 10a within the movement zone 104, it is contemplated that only the brakes required to keep the suspension arm assembly 10a within the movement zone 104 would be braked. It is contemplated that the brake system could be provided that allows only one way movement once the border of the movement zone 104 is met at the motion limit zone 104' or abutment safety zone 104" in the illustrated example. Alternatively, it is contemplated that the brake system could be applied and then released after a predetermined interval (e.g., 500 ms) to allow the suspension arm assembly 10a to be moved away from the walls 102'.

Although particular preferred embodiments of the invention have been disclosed in detail for illustrative purposes, it will be recognized that variations or modifications of the disclosed apparatus, including the rearrangement of parts, lie within the scope of the present invention. For example, the first embodiment and the second embodiment of the suspension arm assembly can be combined in a single assembly such that brakes will be applied when the arms of the suspension arm assembly are aligned as discussed above in the first embodiment of the suspension arm assembly and when the suspension arm assembly moves into the motion limit zone or the abutment safety zone as discussed above in the second embodiment of the suspension arm assembly.

What is claimed is:

1. A medical device assembly comprising:
a support member;
a first arm rotatably connected to the support member at a first rotary joint having a first rotational axis;
a second arm rotatably connected to the first arm at a second rotary joint having a second rotational axis that is parallel to the first rotational axis;
a medical unit connected to an end of the second arm opposite the first arm;
an angle detector located at the second rotary joint and configured to monitor an angle of the first arm relative to the second arm; and
a braking system comprising a brake located at the first rotary joint and a control system comprising one or more processors configured to:
receive one or more signals from the angle detector, and
in response to receiving a signal from the angle detector indicative of the angle detector detecting that the first arm and the second arm are substantially aligned, control the braking system to prevent rotation of the first arm about the first rotary joint while the second arm remains free to rotate relative to the first arm about the second rotary joint.

2. The medical device assembly of claim 1, wherein:
the first arm and the second arm are substantially aligned when an angle between the first arm and the second arm is within a selected amount above or below 180°.

3. The medical device assembly of claim 1, wherein:
the first arm and the second arm are substantially aligned when an angle between the first arm and the second arm is within a selected amount above or below 0°.

4. The medical device assembly of claim 3, wherein:
the first arm and the second arm are also substantially aligned when the angle between the first arm and the second arm is within a selected amount above or below 180°.

5. The medical device assembly of claim 1, wherein:
the medical unit is powered.

6. The medical device assembly of claim 5, wherein:
the powered medical unit is a surgical light.

7. The medical device assembly of claim 1, wherein the angle detector is a position sensor for sensing an angle between the first arm and the second arm.

8. The medical device assembly of claim 1, wherein the angle detector comprises a switch that switches when the first arm reaches a predetermined angular position relative to the second arm.

9. The medical device assembly of claim 1, wherein the angle detector is configured to measure the angle of the first arm relative to the second arm.

10. A medical device assembly comprising:
a ceiling support member;
a substantially linear first arm having a first arm first end and a first arm second end, the first arm first end of the substantially linear first arm being rotatably connected to the ceiling support member at a first rotary joint for allowing the substantially linear first arm to rotate about a first substantially vertical axis;

a substantially linear second arm having a second arm first end and a second arm second end, the second arm first end of the substantially linear second arm being rotatably connected to the substantially linear first arm at a second rotary joint for allowing the substantially linear second arm to rotate about a substantially vertical second axis;
an angle detector located at the second rotary joint and configured to monitor an angle of the substantially linear first arm relative to the substantially linear second arm; and
a braking system comprising a brake located at the first rotary joint; and one or more processors configured to: receive one or more signals from the angle detector, and in response to receiving a signal from the angle detector indicative of the angle detector detecting that the substantially linear first arm and the substantially linear second arm are substantially aligned such that a first line extending between the first arm first end and the first arm second end of the substantially linear first arm is substantially parallel with a second line extending between the second arm first end and the second arm second end of the substantially linear second arm, control the braking system to prevent rotation of the substantially linear first arm about the first substantially vertical axis while the second arm remains free to rotate relative to the first arm about the second rotary joint.

11. The medical device assembly of claim 10, wherein:
the substantially linear first arm and the substantially linear second arm are substantially aligned when an angle between the substantially linear first arm and the substantially linear second arm is within a selected amount above or below 180°.

12. The medical device assembly of claim 11, wherein:
the selected amount is less than or equal to 10°.

13. The medical device assembly of claim 12, wherein:
the selected amount is less than or equal to 5°.

14. The medical device assembly of claim 10, wherein:
the substantially linear first arm and the substantially linear second arm are substantially aligned when an angle between the substantially linear first arm and the substantially linear second arm is within a selected amount above or below 0°.

15. The medical device assembly of claim 14, wherein:
the selected amount is less than or equal to 10°.

16. The medical device assembly of claim 15, wherein:
the selected amount is less than or equal to 5°.

17. The medical device assembly of claim 14, wherein:
the substantially linear first arm and the substantially linear second arm are substantially aligned when an angle between the substantially linear first arm and the substantially linear second arm is within the selected amount above or below 180°.

18. The medical device assembly of claim 17, wherein:
the selected amount is less than or equal to 10°.

19. The medical device assembly of claim 18, wherein:
the selected amount is less than or equal to 5°.

20. The medical device assembly of claim 10, further including:
a powered medical unit connected to the second arm second end of the substantially linear second arm.

21. The medical device assembly of claim 20, wherein:
the powered medical unit is a surgical light.

22. A method of moving a surgical device assembly comprising:
monitoring a position of a substantially linear first arm relative to a substantially linear second arm with an angle detector, the first arm being rotatably connected to a ceiling support member at a first rotary joint having a substantially vertical rotation axis, and the second arm being rotatably connected to the substantially linear first arm at a second rotary joint having a substantially vertical second axis;
preventing the substantially linear first arm from rotating about the first substantially vertical axis with a braking system in response to the angle detector detecting that the substantially linear first arm and the substantially linear second arm are substantially aligned such that a first line extending between first and second ends of the first arm is substantially parallel with a second line extending between first and second ends of the second arm of the substantially linear second arm; and
allowing the substantially linear first arm to rotate about the first substantially vertical axis when the substantially linear first arm and the substantially linear second arm are not substantially aligned.

23. The method of claim 22, wherein:
the substantially linear first arm and the substantially linear second arm are substantially aligned when an angle between the substantially linear first arm and the substantially linear second arm is within a selected amount above or below 180° or above or below 0°.

24. The method of claim 23, wherein:
the selected amount is less than or equal to 10°.

25. The method of claim 24, wherein:
the selected amount is less than or equal to 5°.

26. A method of moving a surgical device assembly comprising:
providing a support member;
providing a support arm assembly having a proximal end and a distal end, the support arm assembly including a plurality of support arms;
rotatably connecting the proximal end of the support arm assembly to the support member for rotation about a proximal pivot joint axis;
connecting the distal end of the support arm to a medical unit;
rotatably connecting each of the support arms to at least one of the support arms, each of the support arms being rotatably connected to the at least one of the support arms for rotation about an intermediate pivot joint axis;
measuring a proximal angle of the support arm assembly relative to the support member about the proximal pivot joint axis;
measuring each intermediate angle of each of the support arms about each intermediate pivot joint axis; and
preventing the support arm assembly from rotating about the proximal pivot joint axis and the support arms from rotating about each intermediate pivot joint axis when at least the proximal angle and each intermediate angle indicate that the medical unit is at a certain location.

27. The method of claim 26, wherein:
preventing the support arm assembly from rotating about the proximal pivot joint axis and the support arms from rotating about each intermediate pivot joint axis occurs when the proximal angle and each intermediate angle indicate that the support arms are substantially linearly aligned.

28. The method of claim 27, wherein:
the plurality of support arms includes two support arms, with a single intermediate pivot joint axis existing between the two support arms.

29. The method of claim 26, wherein:
preventing the support arm assembly from rotating about the proximal pivot joint axis and the support arms from rotating about each intermediate pivot joint axis occurs when the medical unit is about to pass outside of a movement zone.

30. The method of claim 29, wherein:
the plurality of support arms includes two support arms, with a single intermediate pivot joint axis existing between the two support arms.

31. The method of claim 29, further including:
rotatably connecting the distal end of the support arm assembly to the medical unit for rotation about a distal pivot joint axis;
measuring a distal angle of the support arm assembly relative to the medical unit about the distal pivot joint axis; and
preventing the support arm assembly from rotating about the proximal pivot joint axis, the support arms from rotating about each intermediate pivot joint axis and the medical unit from rotating about the distal pivot joint axis when the proximal angle, each intermediate angle and the distal angle indicate that the medical unit is at the certain location.

32. The method of claim 29, further including:
programming the movement zone into a control system of the surgical device assembly.

33. The method of claim 29, wherein:
programming the movement zone includes moving the medical unit about a periphery of the movement zone.

34. A medical device assembly comprising:
a support member;
a support arm assembly having a proximal end and a distal end, the support arm assembly including a plurality of support arms;
the proximal end of the support arm assembly being rotatably connected to the support member for rotation about a proximal pivot joint axis;
the distal end of the support arm being connected to a medical unit;
each of the support arms being rotatably connected to at least one of the support arms, each of the support arms being rotatably connected to the at least one of the support arms for rotation about an intermediate pivot joint axis;
a proximal angle measurement system for measuring a proximal angle of the support arm assembly relative to the support member about the proximal pivot joint axis; and
an intermediate angle measurement system for measuring each intermediate angle of each of the support arms about each intermediate pivot joint axis;
wherein the support arm assembly is prevented from rotating about the proximal pivot joint axis and the support arms are prevented from rotating about each intermediate pivot joint axis when at least the proximal angle and each intermediate angle indicate that the medical unit is at a certain location.

35. The medical device assembly of claim 34, wherein:
the support arm assembly is prevented from rotating about the proximal pivot joint axis and the support arms are prevented from rotating about each intermediate pivot joint axis when the proximal angle and each intermediate angle indicate that the support arms are substantially linearly aligned.

36. The medical device assembly of claim 35, wherein:
the plurality of support arms includes two support arms, with a single intermediate pivot joint axis existing between the two support arms.

37. The medical device assembly of claim 34, wherein:
the support arm assembly is prevented from rotating about the proximal pivot joint axis and the support arms are prevented from rotating about each intermediate pivot joint axis when the medical unit is about to pass outside of a movement zone.

38. The medical device assembly of claim 37, wherein:
the plurality of support arms includes two support arms, with a single intermediate pivot joint axis exists between the two support arms.

39. The medical device assembly of claim 37, wherein:
the distal end of the support arm assembly is rotatably connected to the medical unit for rotation about a distal pivot joint axis;
and further including a distal angle measurement system for measuring a distal angle of the support arm assembly relative to the medical unit about the distal pivot joint axis; and
the support arm assembly is prevented rotating about the proximal pivot joint axis, the support arms are prevented from rotating about each intermediate pivot joint axis and the medical unit is prevented from rotating about the distal pivot joint axis when the proximal angle, each intermediate angle and the distal angle indicate that the medical unit is at the certain location.

40. The medical device assembly of claim 37, further including:
a control system of the surgical device assembly having the movement zone programmed therein.

* * * * *